United States Patent [19]
Jenkner et al.

[11] 4,182,706
[45] Jan. 8, 1980

[54] FLAME-RETARDANT AGENTS FOR PHENOLIC RESINS AND PROCESS FOR THEIR PRODUCTION

[75] Inventors: Herbert Jenkner; Robert Strang, both of Cologne, Fed. Rep. of Germany

[73] Assignee: Chemische Fabrik Kalk GmbH, Cologne, Fed. Rep. of Germany

[21] Appl. No.: 906,416

[22] Filed: May 16, 1978

[30] Foreign Application Priority Data

May 14, 1977 [DE] Fed. Rep. of Germany ....... 2721889

[51] Int. Cl.$^2$ .............................................. C08K 5/52
[52] U.S. Cl. .................... 260/45.95 G; 260/45.7 PH; 428/531; 568/649
[58] Field of Search .................... 260/613 B, 45.95 G, 260/45.7 PH, 53 HA; 427/288, 391; 428/530, 531, 921

[56] References Cited

U.S. PATENT DOCUMENTS

| | | | |
|---|---|---|---|
| 2,089,569 | 8/1937 | Orthner et al. | 260/613 B |
| 3,075,944 | 1/1963 | Wick et al. | 260/45.95 G |
| 3,666,617 | 5/1972 | Marciniak | 260/45.7 W |
| 3,749,600 | 7/1973 | Bergman et al. | 260/45.95 G |
| 3,775,355 | 11/1973 | Jellinek et al. | 260/37 EP |
| 4,056,656 | 11/1977 | Franz et al. | 428/530 |

FOREIGN PATENT DOCUMENTS

| | | | |
|---|---|---|---|
| 47-36248 | of 1972 | Japan . | |
| 628497 | 8/1949 | United Kingdom | 568/662 |
| 800215 | 8/1958 | United Kingdom . | |
| 1022878 | 3/1966 | United Kingdom | 568/608 |

*Primary Examiner*—V. P. Hoke
*Attorney, Agent, or Firm*—Millen & White

[57] ABSTRACT

Bromated phenylglycerin ethers, prepared by reacting a brominated phenol with 2,3-epoxypropanol-1 in the presence of an alkali at elevated temperatures, are useful flame retardant agents for phenol resins and phenolic resin laminates when used in amounts of about 3 to 30 parts by weight per 100 parts of resin.

6 Claims, No Drawings

FLAME-RETARDANT AGENTS FOR PHENOLIC RESINS AND PROCESS FOR THEIR PRODUCTION

Phenolic resin laminates are used extensively in commence and industry in the form of hard papers and hard fabrics. The hard papers, for example, have proven themselves as useful insulating materials in power engineering and telecommunications, as well as in electronics. While such phenolic resin laminates are useful in many fields of application, it often is necessary to modify the phenolic resins contained in the laminates to reduce their combustibility.

Various additives have already been described which may be used for the production of difficult combustible phenolic resins and phenolic resin laminates. Thus, for example, the addition of tris-(dibromopropyl)-phosphate to phenolic resins provides resins which exhibit very good flame retardant characteristics. However, while the addition of tris-(dibromopropyl)-phosphate substantially increases the flame retardance of phenolic resins, such addition decreases the electrical insulating properties of phenolic resins to such a point that these phenolic resins may not be used for laminates which are to be used in telecommunications and electronics.

Better results, with respect to the electrical insulating properties of the phenolic resin laminates to be produced, may be achieved by the addition of tribromophenyl-dibromopropyl ethers or of highly bromated diphenyl ethers to the phenolic resins used to impregnate and bend the individual lamina. However, tribromophenyl-dibromopropyl ethers are not soluble in aqueous resol resin solutions and, therefore, it is difficult to effect a homogenous distribution of these fire-retardant components in a phenolic resin mass. Other flame retardant compounds, such as the bromated dimethylhydroxypropyl ethers, which are described in the German Pat. No. OS 21 12 005 as flame retardant components, also are insoluble in aqueous resol resin solutions and, therefore, are difficult to disperse homogenously in the phenolic resins.

Still another group of compounds which are used as flame retardant components for phenolic resins are bromated glycidyl ethers, for example, the bromophenylglycidyl ether, which is described in the Japanese Pat. No. 72 36 248. Such ethers, however, exhibit relatively low thermal stability. Accordingly, in the instances when high processing temperatures are required to form phenolic resin laminates, the bromated glycidyl ethers would be decomposed prematurely.

Thus, prior to the subject invention, there existed the need for a fire-retardant agent for phenolic resins, which agent is soluble in aqueous resol resin mixtures, imparts good flame retardant characteristics to the phenolic resins, does not deteriorate the mechanical and electrical characteristics of the phenolic resins or the phenolic resin laminates that are to be produced, and has a sufficient thermal stability to render the agents useful for conventional laminating processes.

It has now been found that this prior art need for a suitable fire-retardant agent for phenolic resins can be accomplished by the use of nuclear-bromated phenylglycerin ethers as the fire retardant agent for phenolic resin laminates. Mono to pentabromated bromophenylglycerin ethers or their mixtures have been found to be suitable for this purpose.

The production of these bromated phenylglycerin ethers can be illustrated by the production of monobromophenylglycerin ether; this compound being produced by reacting a nuclear-bromated phenol, especially monobromophenol, with 2,3-epoxypropanol-1 and a minor amount of an alkaline material at an elevated temperature. The reaction may be carried out in the presence or absence of a solvent, and, insofar as a solvent is used, suitable solvents include alcohols such as methanol, ethanol, isopropanol, butanol, etc. When a solvent is used, the quantity of solvent may comprise from about 50 to 150 parts by weight per 100 parts by weight of nuclear-bromated phenol. The alkaline material, which may be added to the reaction mixture in a dry, finely powdered state, advantageously comprises sodium hydroxide or potassium hydroxide.

The reaction temperature lies between about 60° and about 120° C.; in the absence of a solvent, this temperature corresponds to the reflux temperature of the reaction mixture. After the reaction has been completed, the bromophenylglycerin ether is obtained as a distillation residue, with the excess epoxypropanol and solvent, if any, having been distilled off.

For use, the bromophenylglycerin ether is dissolved in the resol resin solution of the particular phenolic resin to be produced, whereby 3 to 30 parts by weight of bromophenylglycerin ether, depending on the degree of bromation, are added to the solution per 100 parts by weight of pure resol resin. In many cases, it may be advantageous to add, beside the bromine compound to be used according to the invention, a synergistically acting compound, preferably diphenylcresylphosphate to the resol resin solution. The quantity of such a synergist to be used ranges from about 5 to 20 parts by weight per 100 parts by weight of pure resol resin. This solution then is diluted by the addition of further solvents to such a point that a paper web may be submerged in a bath of the solution, and while pulling it through, may be coated therewith. The paper webs thus coated, are then cut in a manner known per se, and are stacked. These stacks are compressed into laminates in heated presses while the resol resin hardens. Such laminating processes are conventional and need not be discussed in detail herein.

The phenolic resin laminates obtained using the present bromated phenylglycerin ethers exhibit, beside an excellent flame resistance, mechanical and electrical characteristics which, compared to the corresponding values of laminates without the addition of the invention, are changed only little. As a result, prepared in accordance with the present invention, laminates are particularly suitable for use as carriers for printed circuits where, as is well known, very high requirements exist with respect to the mechanical and electric characteristics of the carrier.

The invention will be better understood more fully in view of the following examples:

EXAMPLE 1 (Production of bromophenylglycerine ether with solvent)

In a reaction vessel, there are added, with mixing, 240 parts by weight of ethyl alcohol, 255 parts by weight of bromophenol with a bromine content of 46% by weight, 125 parts by weight of 2,3-epoxypropanol-1 and 2 parts by weight of a finely powdered sodium hydroxide. The mixture is heated, while stirring vigorously, to reflux temperature which lies between 80° and 85° C. and is held at this temperature for 15 hours. The solvent is then distilled off and the residue is washed neutral with water, whereafter the remaining water as well as the excess of epoxypropanol is distilled off at a reduced pressure of about 2 mbar.

The resulting product contains 349 parts by weight of bromophenylglycerin ether in the form of a yellowish-brown, viscous liquid which, after extended standing, partly crystallizes. The reaction product contains 31.7% by weight of bromine and has an OH number of 461. The yield, relative to the bromophenol added to the reaction vessel, is 95.8% of the theoretical yield.

EXAMPLE 2 (Production of bromophenylglycerine ether without solvent)

In a reaction vessel, there are added 4571 parts by weight of bromophenol with a bromine content of 46% by weight and 35% by weight of finely powdered sodium hydroxide. The reactants are heated to a temperature of 80° C. While stirring vigorously, 2251 parts by weight of 2,3-epoxypropanol-1 are added in doses over a period of 3½ hours, whereafter the mixture is kept at a temperature of 90° C. for an additional 3½ hours. The mixture is then cooled to 50° C. and the reaction product is washed neutral with water. Subsequently, the remaining water as well as the excess of epoxypropanol is distilled off at a reduced pressure of about 5 to 7 mbar.

The resulting product contains 6050 parts by weight of bromophenylglycerin ether in the form of a yellowish-brown, viscous liquid, which after extended standing, partly crystallizes. The reaction product contains 31.9% by weight of bromine and has an OH number of 453. The yield, relative to the bromophenol used, amounts to 92.7% of theory.

EXAMPLE 3 (Use of bromophenylglycerin ether as a flame retardant)

To a resol resin solution containing about 72% by weight of resin in a mixture of 95% by weight of water and 5% by weight of methylalcohol, there is added 20 parts by weight of the bromophenylglycerin ether prepared in accordance with Example 1 for every 100 parts of pure resol resin. After a homogenous solution has developed, the latter is diluted with methyl alcohol such that the solution contains about 50% by weight of solid substances. Webs of cotton paper with a weight per unit area of 60 g/m² are saturated with this solution, the webs absorbing about their own weight in resin solution. The saturated webs are hardened for 10 minutes at a temperature of 150° C., are then cut up into sections of suitable size. The cut sections are stacked in layers of 20 pieces. Each stack subsequently is compressed for 90 minutes at a temperature of 150° C. and a pressure of 100 bar to form a laminated product.

Sample pieces of the laminated products are tested, the results of these tests being as follows:

Behavior in case of fire according to ASTM 635:

The requirement of the NEMA Standard Publication LI 1-1965 is fulfilled, which demands less than 15 seconds smoldering time at a burning distance of below 25 mm. Resistance to tracking according to DIN 53 480:

Class KA 1= at 380 V AC voltage and 2 drop-ons per minute the release of excess current occurs between the 1st and 10th drops.

EXAMPLE 4 (Use of diphenylcresylphosphate as synergist)

The procedure of Example 3 was repeated except that 15 parts by weight of diphenylcresylphosphate is added as a synergist per 100 parts of pure resol resin, the same resol resin being used in Examples 3-5.

The results of tests performed on samples of laminated products using a synergistic combination of bromophenylglycerin ether and diphenylcresylphosphate as the fire retardant are as follows:

Behavior in case of fire according to ASTM 635:

Automatic extinguishing after 7 seconds at 20 mm burning distance. Thus the requirement of the NEMA Standard Publication LI 1-1965 is fulfilled, which demands less than 15 seconds smoldering time at a burning distance of below 25 mm.

Behavior in case of fire according to UL 94:

Five times the condition V-O is fulfilled=automatic extinguishing in less than 5 seconds; flaming resin does not drop off.

Breakdown resistance according to DIN 53 481:
10 kV/mm

Resistance to tracking according to DIN 53 480:

Class KA 1= at 380 V AC voltage and 2 drop-ons per minute the release of excess current occurs between the 1st and 10th drops.

The invention being thus described, it will be apparent that certain modifications may be made without departing from the spirit and scope thereof as set forth in the following claims.

What is claimed is:

1. A method for reducing the combustibility of a phenol resin laminate in the form of a hard paper of hard fabric of the type used as an insulating material in power engineering and telecommunications as well as in electronics, comprising homogeneously dispersing in the phenolic resin used to prepare the laminate a flame retarding amount of a nuclear-brominated phenyl glyceryl monoether prepared by reacting a nuclear-brominated phenol with 2,3-epoxypropanol-1 in the presence of an alkaline material at a temperature between about 60° and 120° C.

2. The method of claim 1 wherein said phenolic resin used in the preparation of the phenolic resin laminate comprises a resol resin solution, and wherein 3–30 parts by weight of said nuclear-brominated phenyl glyceryl monoether per 100 parts by weight of pure resol resin are dissolved in said resol resin solution.

3. The method of claim 2, wherein from about 5 to about 20 parts by weight of diphenylcresylphosphate per 100 parts by weight of pure resol resin are added as a synergistically acting flame retardant.

4. The method of claim 1, wherein said nuclear-brominated phenyl glyceryl monoether is selected from the group consisting of mono- to pentabromophenyl glyceryl monoether and mixtures thereof.

5. The method of claim 3, wherein said nuclear-brominated phenyl glyceryl monoether is selected from the group consisting of mono- to pentabromophenyl glyceryl monoether and mixtures thereof.

6. The method of claim 2, wherein said nuclear-brominated phenyl glyceryl monoether is selected from the group consisting of mono- to pentabromophenyl glyceryl monoether and mixtures thereof.

* * * * *